United States Patent
Engel et al.

[11] 3,960,841
[45] June 1, 1976

[54] 3,17,18-TRIHYDROXY-1,3,5(10)-ESTRATRIENES

[75] Inventors: Klaus Engel; Klaus Prezewowsky; Henry Laurent; Yukishige Nishino, all of Berlin, Germany

[73] Assignee: Schering Aktiengesellschaft, Berin & Bergkamen, Germany

[22] Filed: July 12, 1974

[21] Appl. No.: 487,969

[30] Foreign Application Priority Data
July 13, 1973 Germany............................ 2336432

[52] U.S. Cl.................... 260/239.55 R; 260/397.5; 424/238; 424/241
[51] Int. Cl.$^2$........................................... C07J 1/00
[58] Field of Search................. 260/397.5, 239.55 R

[56] References Cited
UNITED STATES PATENTS
3,134,771  5/1964  Ruggieri et al. ............... 260/239.55
3,265,718  8/1966  Christiansen .................... 260/397.5

OTHER PUBLICATIONS
Loke et al., Biochem. Journ., 71, 43 (1959).
Loke et al., Biochem. Biophysica Acta., 26, 230 (1957).
Meyer et al., Journ. Org. Chem., 27, 1130 (1962).

*Primary Examiner*—Ethel G. Love
*Attorney, Agent, or Firm*—Millen, Raptes & White

[57] ABSTRACT

3,17,18-Trihydroxy-1,3,5(10)-estratrienes of the formula

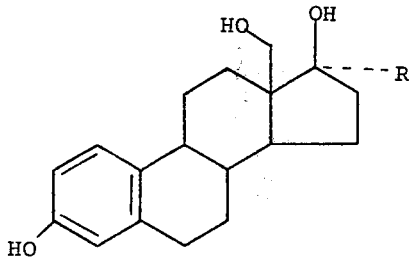

wherein R is H or substituted or unsubstituted saturated or unsaturated hydrocarbon, and esters and ethers thereof, possess strong vaginotropic and only weak utertropic activity and are useful in the treatment of estrogenic deficiency conditions where uteral effects are not desired.

17 Claims, No Drawings

3,17,18-TRIHYDROXY-1,3,5(10)-ESTRATRIENES

BACKGROUND OF THE INVENTION

This invention relates to novel estratrienes. The estrogenic effects of 3,17-dihydroxy-1,3,5(10)-estratrienes and esters and ethers thereof are known. In contradistinction thereto, the compounds of this invention exhibit high vaginotropic but only weak uterotropic activity. 18-Hydroxyestrone and 18-hydroxyestrone diacetate are know [Baldwin et al., J. Chem. Soc. (C) 1968, 2283 ].

SUMMARY OF THE INVENTION

In a composition aspect, this invention relates to 3,17,18-trihydroxy-1,3,5(10)-estratriene and esters and ethers thereof of the general Formula I

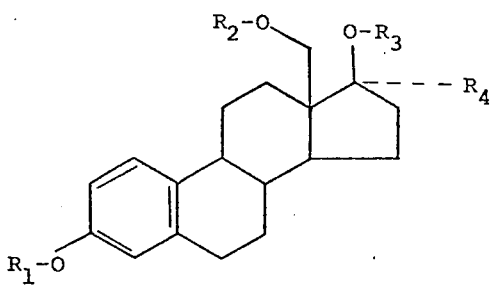

wherein $R_1$, $R_2$, $R_3$, which can be alike or different, are a hydrogen atom, acyl, alkyl, cycloalkyl, or an oxygen-containing saturated heterocyclic group, and $R_4$ is a hydrogen atom or a substituted or unsubstituted saturated or unsaturated hydrocarbon group.

In another composition aspect, this invention relates to pharmaceutical compositions comprising a vaginotropic effective amount per unit dosage of compound of this invention in admixture with a pharmaceutically acceptable carrier.

In a process aspect, this invention relates to a process for the production of the compounds of this invention.

DETAILED DISCUSSION

Suitable acyl groups are those of any physiologically acceptable acid including phosphoric, sulfuric, sulfonic and carboxylic acids. Preferred acyl groups are those of hydrocarbon carboxylic acids of 1–15 carbon atoms, including those of the aliphatic, cycloaliphatic, aromatic and aromatic-aliphatic series. Equivalents of these are those of the heterocyclic series and those which are unsaturated and/or polybasic and/or substituted in the usual manner, e.g., by alkyl, hydroxy, alkoxy, oxo, or amino groups, or halogen atoms.

Examples of suitable carboxylic acids are alkanoic of 1–15, preferably 2–8, carbon atoms, e.g., formic acid, acetic acid, propionic acid, butyric acid, isobutyric acid, valeric acid, isovaleric acid, caproic acid, enanthic acid, caprylic acid, pelargonic acid, undecylic acid, lauric acid, tridecylic acid, myristic acid, trimethylacetic acid, diethylacetic acid, tert.-butylacetic acid, and cycloalkylalkanoic acids wherein cycloalkyl and alkanoic are as defined herein, e.g., cyclopentylacetic acid, cyclohexylacetic acid, cyclohexanecarboxylic acid and arylcarbocyclic carboxylic and arylcarbocyclicalkanoic acids of 7–15, preferably 7–12 carbon atoms, e.g., benzoic and phenylacetic acid. Equivalents of these acids are, e.g., phenoxyacetic acid, mono-, di-, and trichloroacetic acid, aminoacetic acid, diethylaminoacetic acid, piperidinoacetic acid, morpholinoacetic acid, lactic acid, succinic acid, adipic acid, malonic acid, nicotinic acid, isonicotinic acid, and furan-2-carboxylic acid.

Preferred alkyl are lower alkyl of 1–5 carbon atoms, which can be branched in the usual manner. Especially preferred are methyl and ethyl. Equivalents are those substituted in the usual manner, e.g., halogen, preferably by Cl, or alkoxy of 1–4 carbon atoms, e.g., methoxy.

Examples of cycloalkyl are those of 3–8 ring carbon atoms, e.g., cyclopropyl, cyclopentyl, cyclohexyl and cycloheptyl and the corresponding rings bearing, e.g., 1–3 alkyl, preferably methyl groups. Cyclopentyl is preferred.

An example of a saturated oxygen-containing heterocyclic group is tetrahydropyranyl, which is preferred. Equivalents are any other such groups derived from heterocycles with at least one oxygen atom in the ring and perhydrogenated in the oxygen-containing ring, e.g., tetrahydrofuryl.

Examples of hydrocarbon groups are saturated and monounsaturated hydrocarbons of up to 6 carbon atoms, viz., alkyl, alkenyl and alkinyl, e.g., methyl, ethyl, propyl, butyl, pentyl, hexyl, vinyl, ethinyl and propenyl. Equivalents are di-unsubstituted groups, e.g., butadienyl, and butadinynyl and the corresponding hydrocarbon groups bearing the usual, suitable substituents, e.g., halogen, preferably chloro. Preferred hydrocarbon and substituted hydrocarbon groups are ethinyl and chloroethinyl, respectively.

Preferred classes of compounds of this invention are those wherein:

a. $R_1$, $R_2$ and $R_3$, which are alike or different, are hydrogen atoms, alkyl of 1–4 carbon atoms, preferably methyl, alkanoyl of 2–8 carbon atoms, preferably acetoxy, and $R_4$ is a hydrogen atom or, when $R_3$ is a hydrogen atom, ethinyl;

b. those of (a) wherein $R_1$ and $R_2$ are alike, especially those wherein $R_3$ is a hydrogen atom; and c. those of (b) wherein $R_1$ and $R_2$ are acetyl or methyl, preferably acetyl.

The compounds of this invention have a favorable dissociated pharmacological activity, viz., strongly vaginotropic and weakly uterotropic activity, and are thus suitable for the treatment of estrogen deficiency indications where an estrogenic effect on the vaginal epithelium is desired, but an estrogenic effect on the uterus is to be avoided, if at all possible, e.g., in the treatment of estrogenic deficiency in postmenopausal females. Thus, the compounds are useful to delay the aging syndrome in such females, e.g., osteoporosis; depressive mood, peripheric circulatory disorders, cardiac diseases and senile otosclerosis.

This advantageous estrogenic dissociation can be shown, for example, in the sialic acid test on mice. The sialic acid test is conducted as follows:

The mice are ovariectomized. Starting with the 10th day after castration, the animals receive the substance to be tested once daily for 3 days. On the fourth day, the animals are sacrificed. Vagina and uterus are immediately excised and weighed into a test tube for hydrolysis. The determination of the sialic acid is conducted according to Svennerholm [Biochem. Biophys. Acta 24 (1957) 604]. The increase in the organ weights of vagina and uterus in dependence on the dose, as well as the reduction in the sialic acid content are determined, deriving therefrom the relative effective strength of the test compound compared to the standard, estradiol (IV). The relative effectivenesses are converted into a ratio and result in the degree of dissociation, Q. For the standard compound estradiol, Q = 1. Compounds with Q<1 are primarily vaginotropic, and with Q<1 are primarily uterotropic.

In this test, the compounds of this invention have a high dissociation quotient far exceeding that of the standard compounds, as shown in Table 1, using as examples 3,18-diacetoxy-17α-ethinyl-1,3,5(10)-estratrien-17β-ol (I) and 3,18-diacetoxy-1,3,5(10)-estratrien-17β-ol (II), compared with the conventional estrogens 17α-ethinyl-1,3,5(10)-estratriene-3,17β-diol (III) and 1,3,5(10)-estratriene-3,17β-diol (IV).

TABLE 1

| No. | Name | Q = Dissociation Quotient |
|---|---|---|
| I | 3,18-Diacetoxy-17α-ethinyl-1,3,5(10)-estratrien-17β-ol | 2.92 |
| II | 3,18-Diacetoxy-1,3,5(10)-estratrien-17β-ol | 3.15 |
| III | 17α-Ethinyl-1,3,5(10)-estratriene-3,17β-diol | 0.42 |
| IV | 1,3,5(10)-Estratriene-3,17β-diol | 1 |

This invention also relates to pharmaceutical compositions comprising an estratriene of the general Formula I in admixture with a pharmaceutically acceptable carrier.

Such compositions are produced in the usual manner by formulating the effective agents into the desired forms of application, e.g., tablets, dragees, capsules, oral or injectable solutions, employing the usual vehicles, diluents, flavor-ameliorating agents, etc. customary in galenic pharmacy.

The effective agent concentrations in the thus-formulated drugs is dependent on the mode of administration. Thus, a tablet preferably contains 0.01 – 10 mg., solutions for parenteral administration preferably contain 0.1 – 20 mg./ml. of solution.

As will be apparent to those skilled in the art, the dosage of the medicinal agents of this invention can vary with the type of administration and the respectively selected compound. Moreover, the dosage can vary from the patient. In general, the compounds of the present invention are administered at a dosage level which can achieve the desired results without causing any disadvantageous or deleterious side effects. Thus, the compounds are administered, for example, at a dosage level ranging from approximately 0.02 mg. to about 20 mg., although modifications can be made under certain circumstances, so that a dosage level of more than 20 mg., for example up to 50 mg., is employed. However, a dosage level in the range of about 0.05 mg. to approximately 5 mg. is preferred.

According to the process of this invention, compounds of general Formula I, are produced by reducing, in a conventional manner, a dihydroxyestratrien-17-one of the general Formula II

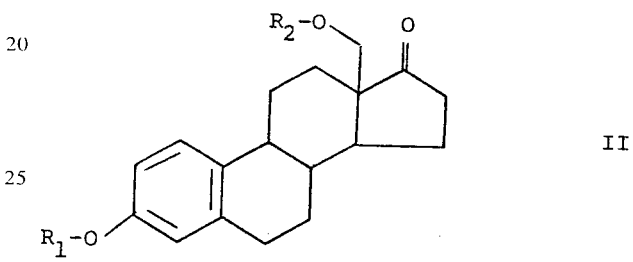

II wherein $R_1$ and $R_2$ have the values given above and optionally thereafter splitting off any $R_1$ or $R_2$ ether or acyl groups or esterifying any or all free hydroxy groups.

To reduce the 17-keto group, conventional processes are suitable. In a preferred mode of operation, the reduction is accomplished, with the 3- and 18-hydroxy groups blocked, i.e., etherified or esterified, with the acyl or ether groups desired in the final product, thus eliminating the necessity of the theoretically possible, but technically more complicated, route of splitting off the blocking group followed by esterification or etherification. Thus, it is most advantageous to select, in the production of the starting compounds, blocking groups for the 3- and/or 18-hydroxy groups, those providing the desired final values for $R_1$ and $R_2$.

The reduction of the 17-keto group can be effected with hydrogen under pressure (for example 50 atmospheres gauge) in the presence of a conventional catalyst, such as, for example, Raney nickel in benzene, at room temperature. The hydrogen atoms also can be transferred to the 17-keto group from metal hydrides. Especially suitable as hydrogen donors are the complex hydrides, e.g., sodium hydridoborate, lithium hydridoaluminate, sodium hydridotrimethoxoborate and lithium hydrido-tri-tert.-butoxoaluminate.

The reduction can also be effected in accordance with known methods with an organometallic compound, thus producing a product wherein $R_4$ is the organic group of the organometallic compound, e.g., an alkylmagnesium halide, such as, for example, methylmagnesium bromide or iodide, an alkenylmagnesium and/or alkenylzinc halide, e.g., vinylmagnesium bromide or allylmagnesium bromide, an alkinylmagnesium halide, such as ethinylmagnesium bromide, propinylmagnesium bromide, or propinylzinc bromide, or an alkali metal acetylide, e.g., potassium acetylide. The organometallic compound employed as the reducing agent can also be formed in situ and reacted with the 17-ketone of Formula II. Thus, for Example, for the reaction with organometallic alkinyl compounds the ketone is treated, in a suitable solvent, with an alkine, chloroalkine, or alkadiyne and an alkali metal, preferably in the presence of a tertiary alcohol or ammonia, optionally under elevated pressure.

Free hydroxy groups can subsequently be esterified or etherified. Esterified or etherified hydroxy groups can be converted into the hydroxy groups.

The acylation in the 3- and 18-positions is conducted preferably with pyridine and the selected acid anhydride at room temperature. For etherification in the 3-position, suitable are the alkylating compounds, preferably diazomethane, dialkyl sulfates, cycloalkyl halogenides and dihydropyran.

To esterify the 17β-hydroxy group of the 3-18-diesters and 3,18-diethers, the steroid is treated, for example, with an acid anhydride in the presence of a strong acid, e.g., p-toluenesulfonic acid, $HClO_4$, or pyridine/acid anhydride under heating. The last-mentioned methods can also be utilized to convert the free trihydroxy compounds directly to the triacylates thereof.

3,18-Diesters and 3,18-diethers can be converted into the corresponding 17-tetrahydropyranyl ethers with dihydropyran in the presence of a strong acid, such as, for example, p-toluenesulfonic acid. The etherification of the 17,18-OH-groups in the compounds of this invention containing an alkyl residue is preferably carried out with alkyl halogenides, e.g., methyl iodide, under gentle conditions, for example, in the presence of $Ag_2O$ in dimethylformamide, or after the preparation of the alkali metal alcoholates, in dimethylformamide with molar equivalent amounts of sodium hydride and subsequent reaction with dimethyl sulfate. The two-last mentioned methods make it likewise possible to etherify all hydroxy groups of the compounds of this invention in one operating step.

The free 3-OH-group and the 18-OH-group can be liberated from 3,18-diacyl-17-tetrahydropyranyl derivatives by alkaline saponification.

The ether splitting step is conducted according to methods known per se. For example, suitable methods are splitting with pyridine hydrochloride or pyridine/concentrated hydrochloric acid at an elevated temperature (180°–220° C.) or with hydrohalic acids in the presence of lower caboxylic acids at temperatures below 150° C. The splitting of tetrahydropyranyl ethers occurs under gentle conditions by the addition of acid.

Among the starting compounds suitable for the preparation of the compounds of this invention are the known 18-hydroxyestrone and 18-hydroxyestrone diacetate. Other starting compounds can be produced analogously to processes known to persons skilled in the art. As examples, there are described in the Preparations hereinafter the preparation of 3,18-bis(tetrahydropyranyloxy)-1,3,5(10)-estratrien-17-one (A); 3,18-bis(methoxy)-1,3,5(10)-estratrien-17-one (B); and 3,18-bis(heptanoyloxy)-1,3,5(10)-estratrien-17-one (C).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperaures are set forth uncorrected in degrees Celsius; unless otherwise indicated, all parts and percentages are by weight.

PREPARATIONS

A. A solution of 900 mg. of 18-hydroxyestrone in 45 ml. of absolute benzene is combined with 1.35 ml. of distilled dihydropyran and 10 mg. of p-toluenesulfonic acid. The solution is agitated for 1.5 hours at room temperature, then washed to neutrality with a sodium bicarbonate solution and water, dried, and evaporated, thus obtaining 850 mg. of 3,18-bis(tetrahydropyranyloxy)-1,3,5(10)-estratrien-17-one as a crude product.

B. 1.5 g. of 18-hydroxyestrone is dissolved in 25 ml. of dimethylformamide and mixed at room temperature with 3.2 ml. of methyl iodide. Thereafter, 6 g. of silver oxide is added in incremental portions and under thorough agitation within 1.5 hours. After 46 hours of agitation, the mixture is diluted with 100 ml. of chloroform, filtered via a porous glass plate with "Celite," the filtrate is washed with water, dried and evaporated, thus producing 0.9 g. of 3,18-dimethoxy-1,3,5(10)-estratrien-17-one as an oily substance.

C. 450 mg. of 18-hydroxyestrone is heated with 3 ml. of pyridine and 3 ml. of enanthic acid anhydride for 1.5 hours to 100° C. After allowing the mixture to stand at room temperature for 15 hours, 15 ml. of water is added dropwise under stirring and cooling, and the reaction product, separated in an oily form, is shaken out with ether after 3 hours. The ether solution is washed successively with dilute sulfuric acid, water, dilute soda solution and water, and dried over sodium sulfate. After evaporation and purification by chromatography, 3-18-bis(heptanoyloxy)-1,3,5(10)-estratrien-17-one is obtained as an oily substance.

EXAMPLE 1

1.8 g. of crude 3,18-bis(tetrahydropyranyloxy)-1,3,5(10)-estratrien-17-one is dissolved in 45 ml. of absolute THF, and the solution is added to a suspension of potassium acetylide in THF (produced by introducing acetylene for one hour into a suspension of 10 g. of potassium tert.-butylate in 135 ml. of absolute THF at −10° C.). After this step, acetylene is furthermore introduced into the reaction mixture for 2.5 hours. The mixture is stirred into ice water/sodium chloride and neutralized with acetic acid; the substance is extracted with ether. After drying the evaporation, 1.8 g. of 3,18-bis(tetrahydropyranyloxy)-17α-ethinyl-1,3,5(10)-estratrien-17β-ol is obtained as a crude product.

EXAMPLE 2

1.8 g. of crude 3,18-bis(tetrahydropyranyloxy)-17α-ethinyl-1,3,5(10)-estratrien-17β-ol is heated to the boiling point with 1.8 g. of oxalic acid in 100 ml. of methanol and a small amount of water. After evaporation under vacuum, the mixture is taken up in ether/methylene chloride and washed neutral. The crude product (1.0 g.) is recrystallized from methanol over carbon, thus obtaining 478 mg. of 17α-ethinyl-1,3,5(10)-estratriene-3,17β,18-triol, m.p. 266° C. (decomposition).

EXAMPLE 3

A solution of 400 mg. of 17α-ethinyl-1,3,5(10)-estratriene-3,17β,18-triol in 3 ml. of pyridine is mixed with 1.5 ml. of acetic anhydride and allowed to stand for 5 hours at room temperature. The mixture is then stirred into ice water, the precipitate is filtered off and taken up in ether. After drying and evaporation, the mixture is purified by chromatography on $SiO_2$, thus obtaining 150 mg. of 3,18-diacetoxy-17α-ethinyl-1,3,5(10)-estratrien-17β-ol in the form of a foam.

NMR: 2.78 (H-1, t, 2 Hz, 1); 3.16 (H-2, d, 1 Hz, 1); 3.24 (H-4, s, 1); 5.64 (H-18, d, 6 Hz, 1); 5.8 (H-18, d, 6 Hz, 1); 7.39 (—C≡CH, s, 1); 7.75 (3-acetate, s, 3); 7.97 (18-acetate, s, 3).

EXAMPLE 4

A solution of 300 mg. of 17α-ethinyl-1,3,5(10)-estratriene-3,17β,18-triol in 2 ml. of pyridine is combined with 1 g. of caproic anhydride and worked up analogously to (C), thus producing 130 mg. of 3,18-bis(hexanoyloxy)-17α-ethinyl-1,3,5(10)-estratrien-17β-ol as an oil.

EXAMPLE 5

A solution of 1.4 g. of 18-hydroxyestrone diacetate in 20 ml. of absolute THF is combined with 2 g. of lithium tri-tert.-butoxyaluminum 3.24 at 10° C. under agitation; the mixture is allowed to react for 10 minutes at room temperature. Then, the mixture is introduced into ice water/NaCl solution and some glacial acetic acid and extracted with ether. The solution is washed, dried, and evaporated. After purification Ilayer chromatography, 700 mg. of 3,18-diacetoxy-1,3,5(10)-estratrien-17β-ol is obtained as a foam.

NMR: 2.78 (H-1, t, 2 Hz, 1); 3.16 (H-2, d, 1 Hz, 1); 3.24 (H-4, s, 1); 6.16 (H-17, t, 4 Hz, 1); 5.65 (H-18, d, 6 Hz, 1); 5.82 (H-18, d, 6 Hz, 1); 7.75 (3-acetate, s, 3); 7.95 (18-acetate, s, 3).

EXAMPLE 6

A solution of 740 mg. of 18-hydroxyestrone diacetate in 8 ml. of absolute THF is combined under ice cooling with 800 mg. of lithium aluminum hydride and agitated for 1 hour at room temperature. Thereafter, 350 mg. of $Na_2CO_3$ in 3.5 ml. of water is added thereto in order to complete the saponification. After 30 minutes of agitation at room temperature, the mixture is dluted with THF and washed with saturated NaCl solution, dried, and evaporated. After purification by layer chromatography, 98 mg. of 18-hydroxyestradiol is produced from acetone, m.p. 231°/233°–235° C.

EXAMPLE 7

250 mg. of 3,18-dimethoxy-1,3,5(10)-estratrien-17-one is ethinylated and worked up as described in Example 1, thus obtaining 230 mg. of 3,18-dimethoxy-17α-ethinyl-1,3,5(10)-estratrien-17β-ol.

EXAMPLE 8

At room temperature, a solution of 1.4 g. of 3,18-bis(heptanoyloxy)-1,3,5(10)-estratrien-17-one in 60 ml. of absolute THF is added dropwise to an ethinyl Grignard solution in THF (produced from 5.6 g of Mg and 15.7 ml. of ethyl bromide in 78 ml. of absolute THF and saturation of the solution with acetylene under ice cooling). After 20 hours of agitation under $N_2$ at 70° C., the mixture is diluted with ether and decomposed by adding saturated $NH_4Cl$ solution. The organic phase is washed neutral with $NH_4Cl$ solution and water, dried, and evaporated, and the residue (1.5 g.) is dissolved in 5 ml. of pyridine and heated with 5 ml. of enanthic anhydride for 2 hours to 50° C. Thereafter, 25 ml. of water is added under agitation and cooling. After 1 hour of agitation, the mixture is taken up in ether. The organic phase is washed successively with dilute sulfuric acid, $Na_2CO_3$ solution, and water, dried, and evaporated. After purification by chromatography over silica gel, 3,18-bis(heptanoyloxy)-17α-ethinyl-1,3,5(10)-estratrien-17β-ol is produced.

EXAMPLE 9

400 mg. of 17α-ethinyl-1,3,5(10)-estratriene-3,17β,18-triol is dissolved in 6 ml. of pyridine, combined with 6 ml. of valeric anhydride, and heated to 160° C. under $N_2$ and agitation for 8 hours. The mixture is cooled, water (25 ml.) is added dropwise under cooling, and the mixture is stirred for 1 hour to decompose the anhydride. Then, the oily product is taken up in ether, the solution is washed successively with dilute sulfuric acid, water, $Na_2CO_3$ solution, and water, dried, and evaporated. After purification over silica gel, 3,17β,18-tris(valeryloxy)-17α-ethinyl-1,3,5(10)-estratriene is obtained as an oil.

EXAMPLE 10

300 mg. of 1,3,5(10)-estratriene-3,17β,18-triol is dissolved in 5 ml. of pyridine. The solution is combined with 5 ml. of butyric anhydride and — according to Example 9 — heated and worked up, thus obtaining 3,17β,18-tris(butyryloxy)-1,3,5(10)-estratriene.

EXAMPLE 11

At −70° C., 0.23 g. of sodium is gradually introduced in small pieces into approximately 70–80 ml. of liquid ammonia, after adding a trace of iron(III) nitrate. After the blue color has disappeared, a solution of 3.4 g. of 3,18-dimethoxy-17α-ethinyl-1,3,5(10)-estratrien-17β-ol in 50 ml. of absolute THF is added thereto, and the reaction mixture is stirred for 1 hour. Then, 0.63 ml. of methyl iodide in 5 ml. of absolute THF is added dropwise. After 3 hours of agitation, the mixture is poured on ice and acidified with acetic acid. The filtered-off precipitate is taken up in ether; the solution is washed neutral with water, dried, and evaporated. After chromatography over silica gel, 3,17β,18-trimethoxy-17α-ethinyl-1,3,5(10)-estratriene is obtained.

EXAMPLE 12

Analogously to (B), 1 g. of 18-hydroxyestradiol is converted into 650 mg. of 3,17β,18-trimethoxy-1,3,5(10)-estratriene.

EXAMPLE 13

350 mg. of 3,18-bis(tetrahydropyranyloxy)-17α-ethinyl-1,3,5(10)-estratrien-17β-ol is heated in 2 ml. of pyridine with 1 ml. of acetic anhydride for 7 hours to 120° C. under nitrogen. The reaction mixture is then introduced into ice water, agitated for 1 hour, and extracted with ether. The ether phase is washed neutral, dried, and evaporated. The thus-obtained residue of 3,18-bis(tetrahydropyranyloxy)-17β-acetoxy-17α-ethinyl-1,3,5(10)-estratriene is heated for 1 hour in 5 ml. of water and 5 ml. of methanol with 0.5 g. of oxalic acid to the boiling point in order to split the ether. After the mixture has been taken up in ether, the solution is washed neutral with water, dried, and evaporated. After chromatographic purification, 17β-acetoxy-17α-ethinyl-1,3,5(10)-estratriene-3,18-diol is obtained.

EXAMPLE 14

400 mg. of 3,18-bis)tetrahydropyranyloxy)-1,3,5(10)-estratrien-17-one is mixed, in 4 ml. of absolute THF, at 0° C. with 400 mg. of lithium tri-tert.-butoxyaluminum hydride and stirred for 30 minutes at room temperature. After the mixture has been poured into water, it is extracted with ether. The ether phase is washed neutral with water, dried, and evaporated. The residue of crude 3,18-bis(tetrahydropyranyloxy)-1,3,5(10)-estratrien-17$\beta$-ol is heated in 1 ml. of pyridine with 1 ml. of acetic anhydride for 30 minutes to 100° C. The mixture is then introduced into water, stirred for 45 minutes, extracted with ether, and washed neutral with water. After drying and evaporation, crude 3,18-bis(tetrahydropyranyloxy)-17$\beta$-acetoxy-1,3,5(10)-estratriene is obtained, which is heated to the boiling point in 4 ml. of methanol with 4 ml. of water and 0.4 g. of oxalic acid. After 1 hour, the mixture is taken up in ether, washed neutral with water, dried, and evaporated. After purification by chromatography over silica gel, 17$\beta$-acetoxy-1,3,5(10)-estratriene-3,18-diol is obtained.

EXAMPLE 15

At −70° C. 0.12 g. of sodium is gradually introduced in small pieces into approximately 40 ml. of liquid ammonia, after adding a trace of iron(III) nitrate. After the blue color has disappeared, a solution of 2.4 g of 3,18-bis(tetrahydropyranyloxy)-17$\alpha$-ethinyl-1,3,5(10)-estratrien-17$\beta$-ol in 20 ml. of absolute THF is added thereto and the mixture stirred for 1 hour. Thereafter, 0.3 ml. of methyl iodide in 2 ml. of THF is added dropwise. After 3 hours of agitation, the mixture is poured on ice, acidified with acetic acid, taken up in ether, washed netural with water, dried, and evaporated. The residue of 17$\beta$-methoxy-3,18-bis(tetrahydropyranyloxy)-17$\alpha$-ethinyl-1,3,5(10)-estratriene is heated to the boiling point for 1 hour in 20 ml. of methanol with 10 ml. of water and 2.4 g. of oxalic acid; the mixture is then taken up in ether, washed neutral with water, dried, and evaporated. After chromatographic purification, 17$\beta$-methoxy- 17$\beta$-ethinyl-1,3,5(10)-estratriene-3,18-diol is produced.

EXAMPLE 16

A solution of 450 mg. of 3,18-bis(tetrahydropyranyloxy)-1,3,5(10)-estratrien-17-one in 10 ml. of absolute THF is combined at 0° C. with 500 mg. of lithium tri-tert.-butoxyaluminum hydride and agitated for one-half hour at room temperature. Then, the mixture is poured into ice water, taken up in ether, washed neutral with water, dried, and evaporated. The residue of crude 3,18-bis(tetrahydropyranyloxy)-1,3,5(10)-estratrien-17$\beta$-ol is dissolved in 5 ml. of DMF, and under N$_2$ 100 mg. of sodium hydride (50% suspension in oil) is added thereto. After 1 hour of agitation at room temperature, 0.19 ml. of dimethyl sulfate is added. The mixture is stirred for another hour and then introduced into water. After extraction with ether, the organic phase is washed with water and dried. The residue of 3,18-bis(tetrahydropyranyloxy)-17$\beta$-methoxy-1,3,5(10)-estratriene remaining after evaporation is heated to the boiling point in 4 ml. of methanol with 4 ml. of water and 0.4 g. of oxalic acid. After 1 hour, the mixture is taken up in ether, washed neutral with water, dried, and evaporated, and after purification by chromatography over silica gel, 3,18-dihydroxy-17$\beta$-methoxy-1,3,5(10)-estratriene is produced.

EXAMPLE 17

350 mg. of 17$\alpha$-ethinyl-1,3,5(10)-estratriene-3,17$\beta$,18-triol is reacted analogously to (A), yielding 250 mg. of 3,17$\beta$,18-tris(tetrahydropyranyloxy)-17$\alpha$-ethinyl-1,3,5(10)-estratriene.

EXAMPLE 18

940 mg. of 17$\alpha$-ethinyl-1,3,5(10)-estratriene-3,17$\beta$,18-triol is heated for 5 hours to the boiling point in 30 ml. of ethanol under N$_2$ with 1.4 ml. of cyclopentyl bromide and 1.25 g. of potassium carbonate. After precipitation into ice water, the mixture is taken up in ether, the organic phase is washed, dried, and evaporated, yielding after purification by chromatography on silica gel 3-cyclopentyloxy-17$\alpha$-ethinyl-1,3,5(10)-estratriene-17$\beta$,18-diol.

EXAMPLE 19

450 mg. of 3-cyclopentyloxy-17$\alpha$-ethinyl-1,3,5(10)-estratriene-17$\beta$,18-diol is heated overnight to the boiling point in 5 ml. of pyridine with 3 ml. of acetic anhydride under a nitrogen atmosphere. The mixture is then poured into ice water, the precipitate is filtered off, and the residue is taken up in ether. The solution is washed neutral, dried, and evaporated. The residue remaining from the evaporation is purified on silica gel, thus obtaining 3-cyclopentyloxy-17$\beta$,18-diacetoxy-17$\alpha$-ethinyl-1,3,5(10)-estratriene.

EXAMPLE 20

350 mg. of 1,3,5(10)-estratriene-3,17$\beta$,18-triol in 10 ml. of ethanol is heated for 5 hours to the boiling point under N$_2$ with 0.5 ml. of cyclopentyl bromide and 0.5 g. of potassium carbonate. After the mixture has been worked up and purified analogously to Example 18, 3-cyclopentyloxy-1,3,5(10)-estratriene-17$\beta$,18-diol is obtained.

EXAMPLE 21

400 mg. of 3-cyclopentyloxy-1,3,5(10)-estratriene-17$\beta$,18-diol is reacted analogously Example 19 with acetic anhydride, yielding 3-cyclopentyloxy-17$\beta$,18-diacetoxy-1,3,5(10)-estratriene.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 3,17,18-trihydroxy-1,3,5(10)-estratriene or ester or ether thereof of the formula

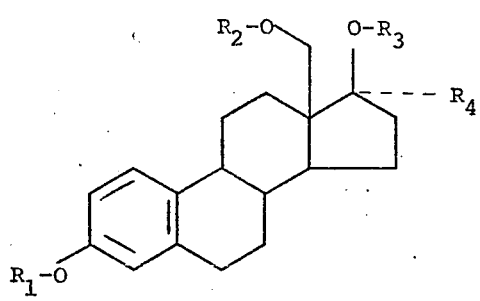

wherein

R$_1$, R$_2$ and R$_3$ each are a hydrogen atom, hydrocarbon acyl of 1–15 carbon atoms, alkyl of 1–5 carbon atoms, cycloalkyl of 3–8 ring atoms or tetrahydropyranyl, and R$_4$ is a monounsaturated aliphatic hydrocarbon of 1–6 carbon atoms.

2. A compound of claim 1 wherein R$_4$ is ethinyl.

3. A compound of claim 1, 3,18-bis(tetrahydropyranyloxy)-17α-ethinyl-1,3,5(10)-estratrien-17β-ol.

4. A compound of claim 1, 17α-ethinyl-1,3,5(10)-estratriene-3,17β,18-triol.

5. A compound of claim 1, 3,18-diacetoxy-17α-ethinyl-1,3,5(10)-estratrien-17β-ol.

6. A compound of claim 1, 3,18-bis(hexanoyloxy)-17α-ethinyl-1,3,5(10)-estratrien-17β-ol.

7. A compound of claim 1, 3,18-dimethoxy-17α-ethinyl-1,3,5(10)-estratrien-17β-ol.

8. A compound of claim 1, 3,18-bis(heptanoyloxy)-17α-ethinyl-1,3,5(10)-estratrien-17β-ol.

9. A compound of claim 1, 3,17β,18-tris(valeryloxy)-17α-ethinyl-1,3,5(10)-estratriene.

10. A compound of claim 1, 3,17β,18-trimethoxy-17α-ethinyl-1,3,5(10)-estratriene.

11. A compound of claim 1, 3,18-bis(tetrahydropyranyloxy)-17β-acetoxy-17α-ethinyl-1,3,5(10)-estratriene.

12. A compound of claim 1, 17β-acetoxy-17α-ethinyl-1,3,5(10)-estratriene-3,18-diol.

13. A compound of claim 1, 17β-methoxy-3,18-bis(tetrahydropyranyloxy)-17α-ethinyl-1,3,5(10)-estratriene.

14. A compound of claim 1, 17β-methoxy-17α-ethinyl-1,3,5(10)-estratriene-3,18-diol.

15. A compound of claim 1, 3,17β,18-tris(tetrahydropyranyloxy)-17α-ethinyl-1,3,5(10)-estratriene.

16. A compound of claim 1, 3-cyclopentyloxy-17α-ethinyl-1,3,5(10)-estratriene-17β,18-diol.

17. A compound of claim 1, 3-cyclopentyloxy-17β,18-diacetoxy-17α-ethinyl-1,3,5(10)-estratriene.

* * * * *